United States Patent
Minato et al.

(10) Patent No.: US 9,619,877 B2
(45) Date of Patent: *Apr. 11, 2017

(54) IMAGE EXAMINATION METHOD AND IMAGE EXAMINATION APPARATUS

(75) Inventors: Yoshihisa Minato, Kyoto (JP); Yukiko Yanagawa, Nara (JP)

(73) Assignee: OMRON Corporation, Kyoto (JP)

( * ) Notice: Subject to any disclaimer, the term of this patent is extended or adjusted under 35 U.S.C. 154(b) by 7 days.

This patent is subject to a terminal disclaimer.

(21) Appl. No.: 14/370,601

(22) PCT Filed: Sep. 14, 2012

(86) PCT No.: PCT/JP2012/073686
§ 371 (c)(1),
(2), (4) Date: Oct. 10, 2014

(87) PCT Pub. No.: WO2013/111373
PCT Pub. Date: Aug. 1, 2013

(65) Prior Publication Data
US 2015/0117750 A1    Apr. 30, 2015

(30) Foreign Application Priority Data
Jan. 27, 2012    (JP) ................... 2012-015810

(51) Int. Cl.
*G06T 7/00*    (2006.01)
*G01N 21/88*    (2006.01)

(52) U.S. Cl.
CPC .......... *G06T 7/0004* (2013.01); *G01N 21/88* (2013.01); *G06T 7/001* (2013.01); *G06T 7/0081* (2013.01);
(Continued)

(58) Field of Classification Search
CPC .......... G06K 9/00449; G06K 9/3233
See application file for complete search history.

(56) References Cited

U.S. PATENT DOCUMENTS

| | | | |
|---|---|---|---|
| 9,269,134 B2 * | 2/2016 | Minato | G06T 7/0004 |
| 2006/0018531 A1 | 1/2006 | Murakami et al. | |
| 2007/0093987 A1 * | 4/2007 | Iida | G05B 23/024 |
| | | | 702/183 |

FOREIGN PATENT DOCUMENTS

| | | | |
|---|---|---|---|
| JP | 2000-163579 | * | 6/2000 |
| JP | 2000-163579 A | | 6/2000 |

(Continued)

OTHER PUBLICATIONS

Yuri Y. Boykov Marie-Pierre Jolly; "interactive graph cuts for optimal boundary &region segmentation of objects in N-D images."; Proceedings of "Internation Conference on Computer Vision", Vancouver, Canada, Jul. 2001.*

(Continued)

*Primary Examiner* — Siamak Harandi
*Assistant Examiner* — Shaghayegh Azima
(74) *Attorney, Agent, or Firm* — Osha Liang LLP

(57) ABSTRACT

An image examination method includes an acquisition step of acquiring a to-be-examined object image obtained by capturing an image of a to-be-examined object, a setting reading step of reading an examination region definition information from a storage device in which the examination region definition information is previously stored, an examination region extracting step of extracting a portion constituting the examination region as an examination region image from the to-be-examined object image based on the examination region definition information, and an examination process step of examining the to-be-examined object by analyzing the examination region image. The examination region definition information is a parameter used as a constraint condition in an optimum solution search process.

11 Claims, 6 Drawing Sheets

(52) U.S. Cl.
CPC .......... G06T 7/0083 (2013.01); G06T 7/0087 (2013.01); G06T 7/0097 (2013.01); *G06T 2200/24* (2013.01); *G06T 2207/10024* (2013.01); *G06T 2207/20076* (2013.01); *G06T 2207/20092* (2013.01); *G06T 2207/20144* (2013.01); *G06T 2207/30164* (2013.01)

(56) References Cited

FOREIGN PATENT DOCUMENTS

| | | |
|---|---|---|
| JP | 2006-58284 A | 3/2006 |
| JP | 2008-139085 A | 6/2008 |

OTHER PUBLICATIONS

International Search Report for corresponding International Application No. PCT/JP2012/073686, mailed Dec. 25, 2012 (2 pages).
Boykov, Y., et al.; "Interactive Graph Cuts for Optimal Boundary & Region Segmentation of Objects in N-D Images;" Proceedings of "Internation Conference on Computer Vision," vol. 1, Vancouver, Canada; Jul. 2001 pp. 105-112 (8 pages).
Tomoyuki Nagahashi et al; "Heikatsuka Shori no Kurikaeshi ni yoru Gazo Segmentation no Tameno Graph Cut" ("Iterated Graph Cuts by Multi-level Smoothing for Image Segmentation"); Dai 10 Kai Meeting on Image Recognition and Understanding (MIRU2007), 2007, 07, pp. 241 to 248 (8 pages) (International Search Report previously cited).

\* cited by examiner

⬇ Specify button unit 21 as background color

⬇ Increase priority for edge in order to exclude hinge unit 20

Confirm examination region

IMAGE EXAMINATION METHOD AND IMAGE EXAMINATION APPARATUS

BACKGROUND

Technical Field

The present invention relates to an image examination apparatus that performs appearance examination using an image.

Related Art

The image examination apparatus that performs the appearance examination using the image is widely used for the purpose of automation and labor-saving of the examination in a production line. There are various kinds and techniques of the appearance examination. In a basic configuration, an image sensor (camera) captures an image of a to-be-examined object, a portion constituting an examination region is extracted from the obtained image, and a feature of the image of the examination region is analyzed and evaluated to perform an intended examination (for example, non-defective/defective determination, assortment, and information acquisition).

In this kind of image examination apparatus, it is necessary to perform preparatory work such as a setting of the examination region before an examination process is started. In a general apparatus, a dedicated tool is prepared in order to set the examination region, and a user can set the proper examination region according to the to-be-examined object or an examination purpose using the tool. However, the conventional tool only has a function of defining the examination region using simple graphics such as a circle and a rectangle or a combination of the graphics. Accordingly, in the case that the to-be-examined object has a complicated shape or a special shape, sometimes the examination region cannot correctly be matched with a contour of the to-be-examined object. Even if the contour of the to-be-examined object can be expressed by the combination of the simple graphics, it takes lots of time and work load to set the examination region when the number of combined graphics increases. Nowadays, there is a strong need to shorten setup time in order to improve efficiency in multi-product, small-quantity production, and it is undesirable to take time to set the examination region. At the same time, there is also a strong need to correctly set the examination region only to a portion to be examined in order to respond to complication of a product shape or a sophisticated and diversified examination content, or to improve examination accuracy or reliability.

In the case that the to-be-examined object has an individual difference, or in the case that the to-be-examined object is not aligned, it is more difficult to set the examination region. For example, in the case that a vegetable conveyed on a belt conveyor is examined, there are no vegetables having the same shape, and the vegetable is not correctly aligned. Therefore, a position or an orientation of the examination region in the image depends on the to-be-examined object. When the examination is accurately performed, it is necessary to set the examination region every time in each to-be-examined object, or to correct the previously-set examination region every time. For this reason, the automatic examination cannot be performed. When the examination region is sufficiently narrowed compared with the to-be-examined object, the examination region is hardly influenced by the individual difference and a fluctuation of the position or orientation, so that the automatic examination can be performed using the same examination region. However, in this method, there is a risk of generating omission of the examination because a portion going out of the examination region exists.

Conventionally, a technique of extracting the examination region by binarization or gamut extraction is well known as a technique of automatically setting the examination region. That is, a pixel group corresponding to a previously-set luminance range or gamut is extracted from the image, and the pixel group is set to the examination region. The technique is effective for high luminance or color contrast between a portion (foreground) that should be extracted as the examination region and other portions (background), and the response to the complicated shape and the simplification of setting work may be addressed.

However, when shadow is generated by an influence of lighting in the foreground that should be extracted as the examination region, when the foreground is constructed with various pieces of luminance or various colors, or when a color close to the foreground exists in the background, it is difficult to correctly extract only the foreground by the binarization or the gamut extraction. Nowadays, the sophistication and the diversification of the examination content progress, and frequently there is a little color difference between the background and the foreground, for example, surface examination is performed to only one cutting surface of a molded product, or only one component is examined on a printed board on which many components are mounted. Because the binarization or the gamut extraction is performed in each pixel of the image, the binarization or the gamut extraction is easily influenced by a noise or a fluctuation of the lighting, the pixel is lost in the extracted examination region, and the pixel is selected from the background like an enclave, which results in the examination accuracy being degraded.

In Patent Document 1, a method for setting a position or a size of the examination region from CAD data of a to-be-examined component, a method for recognizing the to-be-examined region by calculating a difference between images before and after the component is mounted, and the like are disclosed as the examination region setting method. The use of these methods can automatically set the examination region. However, these methods cannot widely be applied, but these methods lack general versatility.

Patent Document 1: Japanese Unexamined Patent Publication No. 2006-58284

Non-Patent Document 1: Y. Boykov and M.-P. Jolly, "Interactive Graph Cuts for Optimal Boundary & Region Segmentation of Objects in N-D images", ICCV2001, 01, p. 105 (2001).

SUMMARY

One or more embodiments of the present invention provides a technology for being able to simply and accurately set the examination region even if the to-be-examined object has the complicated shape or the special shape or even if the foreground and background colors are confused with each other. One or more embodiments of the present invention provides a technology for being able to adaptively automatically set the examination region to accurately perform the examination even if the to-be-examined object has the individual difference or even if the position or the orientation of the to-be-examined object is indefinite.

In one or more embodiments of the present invention, a parameter used as a constraint condition in an optimum solution search process is provided as examination region definition information to an image examination apparatus.

During examination of a to-be-examined object, the image examination apparatus separately determines a position and a shape of an examination region in each to-be-examined object by obtaining an optimum solution of the examination region in a to-be-examined object image with the examination region definition information as the constraint condition.

Specifically, an image examination method according to one or more embodiments of the present invention may be performed by an image examination apparatus, and may include: an acquisition step of acquiring a to-be-examined object image obtained by capturing an image of a to-be-examined object; a setting reading step of reading an examination region definition information from a storage device in which the examination region definition information is previously stored; an examination region extracting step of extracting a portion constituting the examination region as an examination region image from the to-be-examined object image based on the examination region definition information; and an examination process step of examining the to-be-examined object by analyzing the examination region image. In the image examination method, the examination region definition information is a parameter used as a constraint condition in an optimum solution search process, and, in the examination region extracting step, a position and a shape of the examination region are separately determined in each to-be-examined object by performing an optimum solution search process of obtaining an optimum solution of the examination region in the to-be-examined object image with the parameter as the constraint condition.

According to the configuration, the position and the shape of the examination region are separately obtained in each to-be-examined object through the optimum solution search process, so that the correct examination region can automatically be set even to the to-be-examined object having the complicated shape or the special shape. Additionally, the examination region can adaptively automatically be set even if the to-be-examined object has the individual difference or even if the position or the orientation of the to-be-examined object is indefinite. The correct examination region can be set according to the to-be-examined object, which allows the examination to be more accurately performed than ever before.

According to one or more embodiments of the present invention, the optimum solution search process is a process of obtaining an optimum solution of the examination region in plural candidate regions, which are of candidate solutions of the examination region, by evaluating both a degree of pixel separation and a degree of edge overlap based on information a color or a luminance of each pixel in the to-be-examined object image and information on an edge included in the to-be-examined object image, the degree of pixel separation being a degree of separation of the color or the luminance between an inside and an outside of each candidate region, the degree of edge overlap being a degree of overlap between a contour of each candidate region and the edge in the to-be-examined object image.

Both the degree of pixel separation of the color or the luminance between the inside and the outside of the examination region and the degree of edge overlap of the contour of each candidate region and the edge of the examination region are comprehensively evaluated using the edge information in addition to the color or luminance information. Therefore, the extraction accuracy of the examination region can be improved compared with the conventional techniques such as the binarization and the gamut extraction.

According to one or more embodiments of the present invention, the examination region definition information includes a balance parameter as the parameter, the balance parameter being used to adjust a weight in evaluating the degree of pixel separation and the degree of edge overlap. Depending on a kind of the to-be-examined object or an image capturing environment, sometimes the separation is easily performed using the color or the luminance, and sometimes the separation is easily performed using the edge information. Accordingly, the use of the balance parameter easily applies the image examination method to various cases, and the extraction accuracy of the examination region and therefore the examination accuracy can be improved.

According to one or more embodiments of the present invention, one of a value of foreground likelihood of the color or the luminance of each pixel inside the candidate region with respect to a representative color or a representative luminance of a foreground, a value of background likelihood of the color or the luminance of each pixel outside the candidate region with respect to a representative color or a representative luminance of a background, and a synthesizing value of both the values is used as the degree of pixel separation in the optimum solution search process.

According to the configuration, it is evaluated that the degree of pixel separation increases with increasing likelihood of the foreground of the pixel in the examination region and with increasing likelihood of the background of the pixel outside the examination region. The color or the luminance, which becomes the representative of the foreground or the background, is defined to search the examination region based on the color or the luminance, which allows the enhancement of the extraction accuracy of the examination region. All the pixels or only some pixels inside the candidate region may be used to calculate the value in which the likelihood of the foreground is evaluated. Similarly, all the pixels or only some pixels outside the candidate region may be used to calculate the value in which the likelihood of the background is evaluated.

According to one or more embodiments of the present invention, the examination region definition information includes information on one of the representative color and the representative luminance of one of the foreground, the background, and the both as the parameter. The extraction accuracy of the examination region can further be enhanced with the parameter as the constraint condition.

In addition to the above parameters, any parameter may be provided as long as the parameter has an influence on the optimum solution search of the examination region. For example, pieces of information expressing a shape, a size, a position in the image, a texture, topology, an adjacent element, and an inclusive element of the examination region are provided as the parameters, and the solution of the examination region may be searched such that a degree of similarity between the feature of the examination region and the features provided by the parameters is also enhanced in addition to the degree of pixel separation and the degree of edge overlap. Thus, the extraction accuracy of the examination region can further be enhanced with various features of the examination region as the constraint conditions.

Before the examination of the to-be-examined object is started, it is necessary to perform a process of generating the examination region definition information and storing the examination region definition information in the storage device (also referred to as a setting process and a teaching process). For example, according to one or more embodiments of the present invention, the process is performed in the following examination region definition information setting step. That is, the examination region definition information setting step may include a step of acquiring a sample image obtained by capturing an image of a sample of the to-be-examined object; a step of receiving input of the parameter from a user; a step of narrowing the parameter being able to obtain a desired examination region in the sample image in a manner that, every time the input of the parameter is received from the user, the optimum solution search process is performed to the sample image while the constraint condition is updated based on the input parameter; and a step of storing the parameter, which is used to be able to obtain the desired examination region in the sample image, in the storage device as the examination region definition information.

An image examination apparatus according to one or more embodiments of the present invention includes a unit performing at least one of the steps or an examination region setting device for the image examination apparatus including at least one of units related to the examination region setting. Additionally, embodiments of the present invention may also be an image examination method or an examination region setting method, in which at least one of the steps is performed, a program configured to cause a computer to perform the image examination method or the examination region setting method, and a storage medium in which the program is stored.

According to one or more embodiments of the present invention, the examination region can simply and accurately be set, even if the to-be-examined object has the complicated shape or the special shape, or even if the foreground and background colors are confused with each other. Additionally, the examination region can adaptively automatically be set to accurately perform the examination, even if the to-be-examined object has the individual difference or even if the position or the orientation of the to-be-examined object is indefinite.

DETAILED DESCRIPTION

Embodiments of the present invention will be described below with reference to the drawings. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

The following embodiments relate to an image examination apparatus that perform an appearance examination using an image and an examination region setting device that supports work to produce examination region definition information provided to the image examination apparatus.

The image examination apparatus is suitably used in application to continuously examine many articles in an automatic or semi-automatic manner in an FA production line or the like. In the image examination apparatus of one or more embodiments of the present invention, irrespective of a kind of the article to be examined, an examination region is adaptively determined to perform the examination in each to-be-examined object using an original image captured by an image sensor. Therefore, particularly the image examination apparatus of one or more embodiments of the present invention can suitably be applied to the case that a position and a shape of the examination region in the original image fluctuate in each to-be-examined object. Although there are various objects and examination items of the appearance examination, the examination region setting device of one or more embodiments of the present invention can suitably be applied to any examination. In one or more embodiments of the present invention, the examination region setting device is mounted as a function (setting tool) of the image examination apparatus. Alternatively, the image examination apparatus and the examination region setting device may separately be configured.

(Image Examination Apparatus)

Figure 1:
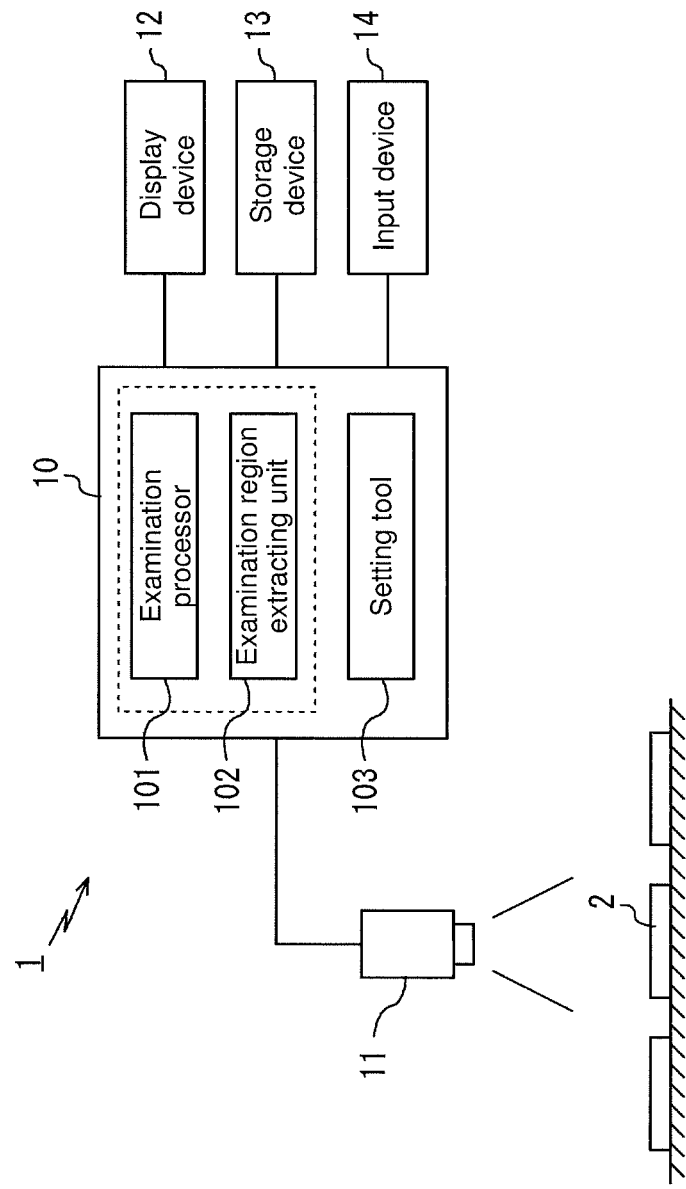
FIG. 1 is a view schematically illustrating a configuration of an image examination apparatus.

FIG. 1 schematically illustrates a configuration of an image examination apparatus. Image examination apparatus 1 is a system that performs the appearance examination of to-be-examined object 2 conveyed on a conveyance path.

As illustrated in FIG. 1, image examination apparatus 1 includes pieces of hardware such as apparatus body 10, image sensor 11, display device 12, storage device 13, and input device 14. Image sensor 11 is a device that captures a color or monochrome still image or moving image in apparatus body 10. For example, a digital camera is suitably used as image sensor 11. In the case that a special image (such as an X-ray image and a thermographic image) except a visible light image is examined, a sensor suitable to the image may be used. Display device 12 is one that displays the image captured with image sensor 11, an examination result, and a GUI screen related to an examination process or a setting process. For example, liquid crystal display can be used as display device 12. Storage device 13 is one in which various pieces of setting information (such as the examination region definition information and examination logic) referred to by image examination apparatus 1 in the examination process and the examination result are stored. For example, an HDD, an SSD, a flash memory, and a network storage can be used as storage device 13. Input device 14 is one that is manipulated by a user in order to input an instruction to apparatus body 10. For example, a mouse, a keyboard, a touch panel, and a dedicated console can be used as input device 14.

Apparatus body 10 can be constructed with a computer including a CPU (Central Processing Unit), a main storage device (RAM), and an auxiliary storage device (such as a ROM, an HDD, and an SSD) as hardware. Apparatus body 10 includes examination processor 101, examination region extracting unit 102, and setting tool 103 as the function. Examination processor 101 and examination region extracting unit 102 are the functions related to the examination process, and setting tool 103 is the function of supporting the user to set setting information necessary for the examination process. A computer program stored in the auxiliary storage device or storage device 13 is loaded on the main storage device, and executed by the CPU, thereby implementing these functions. FIG. 1 illustrates only an example of the apparatus configuration. Alternatively, image sensor 11, display device 12, storage device 13, and input device 14 may wholly or partially be integral with apparatus body 10. Apparatus body 10 may be constructed with a computer such as a personal computer and a slate type terminal, a dedicated chip, or an on-board computer.

(Examination Process)

Figure 2:
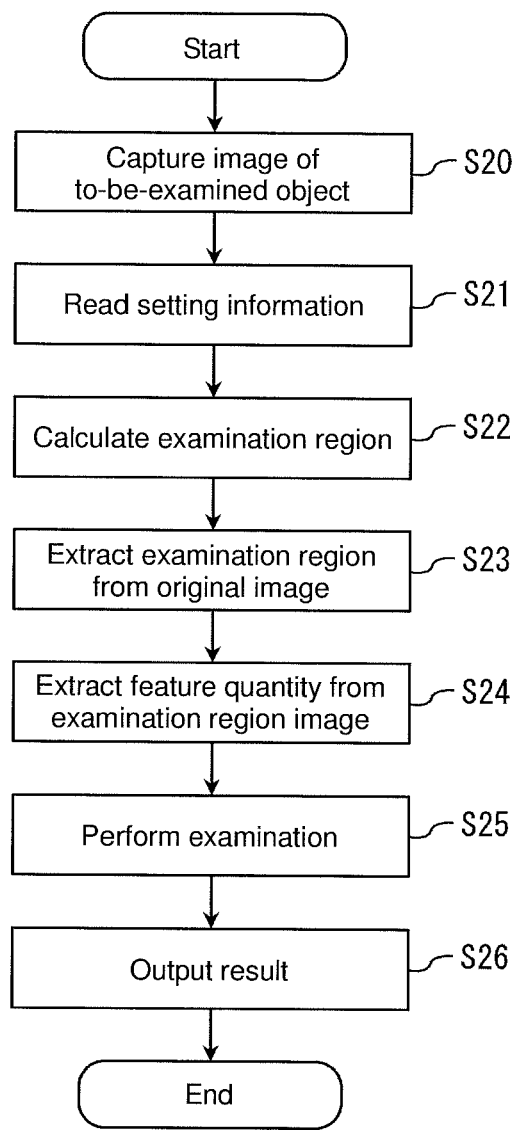
FIG. 2 is a flowchart illustrating a flow of an examination process.
Figure 3:
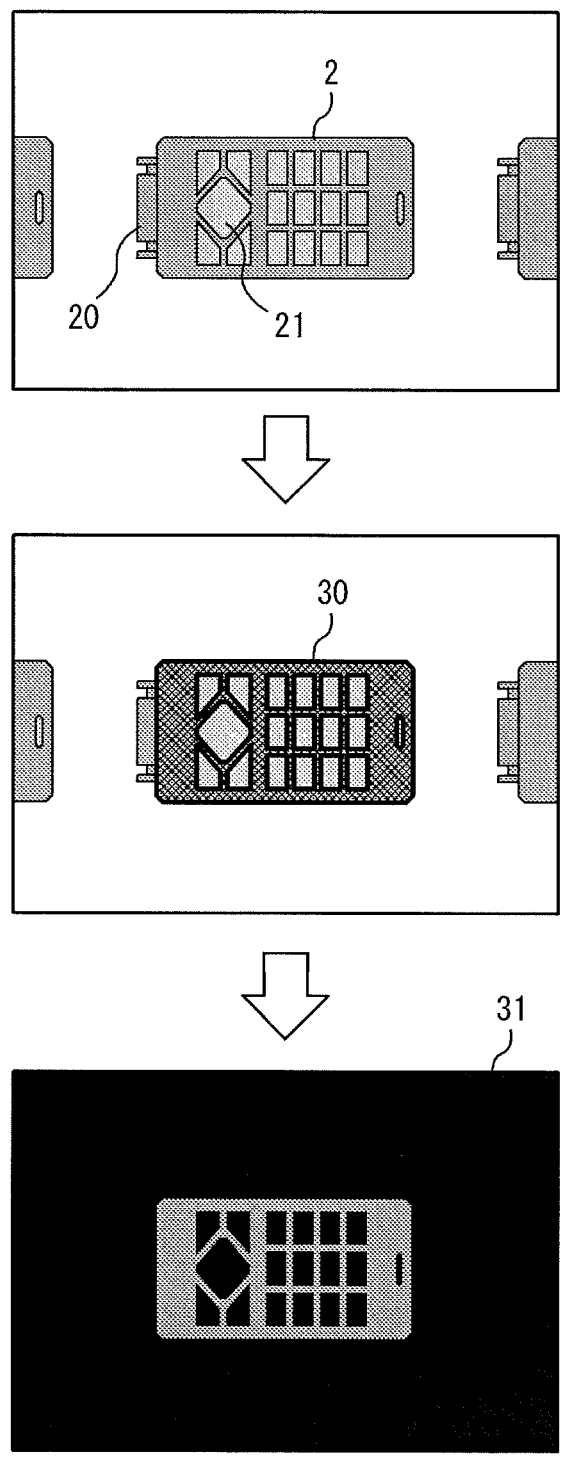
FIG. 3 is a view illustrating an examination region extracting process in the examination process.

Operation related to the examination process of image examination apparatus 1 will be described with reference to FIGS. 2 and 3. FIG. 2 is a flowchart illustrating a flow of the examination process, and FIG. 3 is a view illustrating an examination process extracting process in the examination process. For the sake of convenience, the flow of the examination process will be described by taking an examination for a panel surface of a casing component of a mobile phone as an example.

In Step S20, image sensor 11 captures the image of to-be-examined object 2, and apparatus body 10 takes in image data. The taken-in image (original image; to-be-examined object image) is displayed on display device 12 as needed basis. An upper part of FIG. 3 illustrates an example of the original image. Casing component 2 that becomes an examination target is photographed in a center of the original image, and adjacent casing components located on the conveyance path are partially photographed on both sides of casing component 2.

In Step S21, examination region extracting unit 102 reads the necessary setting information from storage device 13. The setting information includes at least the examination region definition information and the examination logic. As used herein, the examination region definition information means one that defines some parameters used as a constraint condition in an examination region search process at a subsequent stage. An example of the parameter provided as the examination region definition information is described later. The examination logic means one that defines a content of the examination process. For example, a kind of a feature quantity used in the examination, a determination method, and a parameter or a threshold used in feature quantity extracting or determination process correspond to the examination logic.

In Step S22, examination region extracting unit 102 segments original image into a foreground and a background using the examination region definition information (parameter) read in Step S21, and selects the foreground as the examination region. In one or more embodiments of the present invention, using information on an edge included in the original image in addition to information on a color of each pixel of the original image, a degree of pixel separation and a degree of edge overlap are comprehensively evaluated with respect to plural candidate regions that are of candidate solutions of the examination region, and an optimum solution is searched such that both the degree of pixel separation and the degree of edge overlap are enhanced. As used herein, the degree of pixel separation is a degree of color separation between the foreground and the background (that is, between an inside and an outside of a candidate region), and the degree of edge overlap is a degree of overlap between a boundary (that is, a contour of the candidate region) of the foreground and the background and the edge in the original image. The optimum examination region is individually determined through these processes according to an individual difference or an attitude of to-be-examined object 2. The detailed optimum solution search process is described later.

In Step S23, examination region extracting unit 102 extracts the examination region from the original image according to the examination region obtained in Step S22. A middle part of FIG. 3 illustrates a state in which examination region (indicated by cross-hatching) 30 obtained in Step S22 overlaps the original image. It is seen that examination region 30 just overlaps the panel surface of casing component 2. A lower part of FIG. 3 illustrates a state in which an image (examination region image 31) of examination region 30 is extracted from the original image. The conveyance path and the adjacent components, which are photographed around casing component 2, are deleted in examination region image 31. Hinge unit 20 and button unit 21, which are excluded from a target region of surface examination, are also deleted. Obtained examination region image 31 is transferred to examination processor 101.

In Step S24, examination processor 101 extracts the necessary feature quantity from examination region image 31 according to the examination logic. In one or more embodiments of the present invention, the color of each pixel and an average value of the colors of examination region image 31 are extracted as the feature quantity used to examine a flaw and color unevenness of the surface.

In Step S25, examination processor 101 determines existence or non-existence of the flaw and the color unevenness according to the examination logic. For example, in the case that a pixel group in which a color difference for the average value obtained in Step S24 exceeds a threshold, the pixel group can be determined to the flaw or the color unevenness.

In Step S26, examination processor 101 displays the examination result on display device 12, or records the examination result in storage device 13. Therefore, the examination process is completed with respect to one to-be-examined object 2. In a production line, the processes in Steps S20 to S26 of FIG. 2 are repeated in synchronization with timing of conveying to-be-examined object 2 into an angle of view of image sensor 11.

In the appearance examination, desirably only the pixel to be examined is cut out as examination region image 31 in proper quantities. When the background or an excess portion (in the example of FIG. 3, hinge unit 20 or button unit 21) is included in examination region image 31, possibly the pixel of the background or excess portion becomes a noise to degrade examination accuracy. When examination region image 31 is smaller than a range to be examined, possibly the omission of the examination is generated. Therefore, in image examination apparatus 1 of one or more embodiments of the present invention, setting tool 103 is prepared in order to simply produce the examination region definition information cutting out the correct examination region image.

(Examination Region Setting Process)

Figure 4:
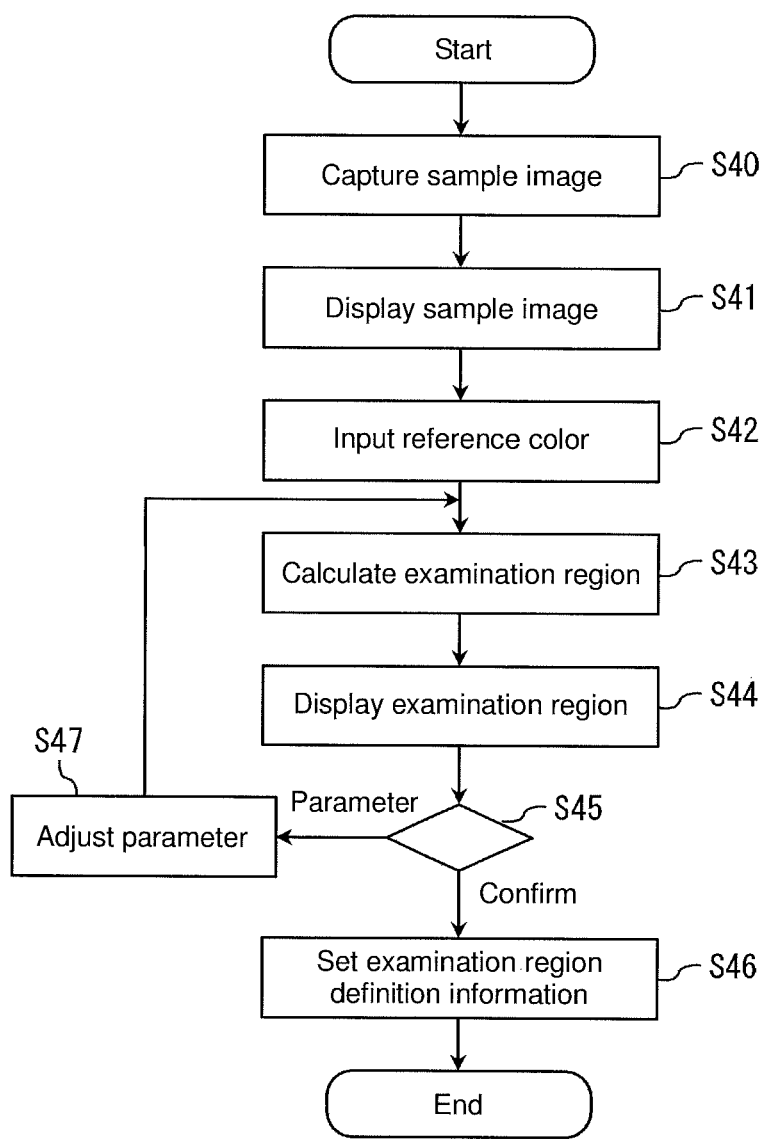
FIG. 4 is a flowchart illustrating a flow of an examination region setting process using setting tool 103.

The function and operation of setting tool 103 will be described with reference to FIGS. 4 and 5. FIG. 4 is a flowchart illustrating a flow of process of setting the examination region definition information using setting tool 103, and FIG. 5 is a view illustrating an example of an examination region setting screen.

Figure 5:
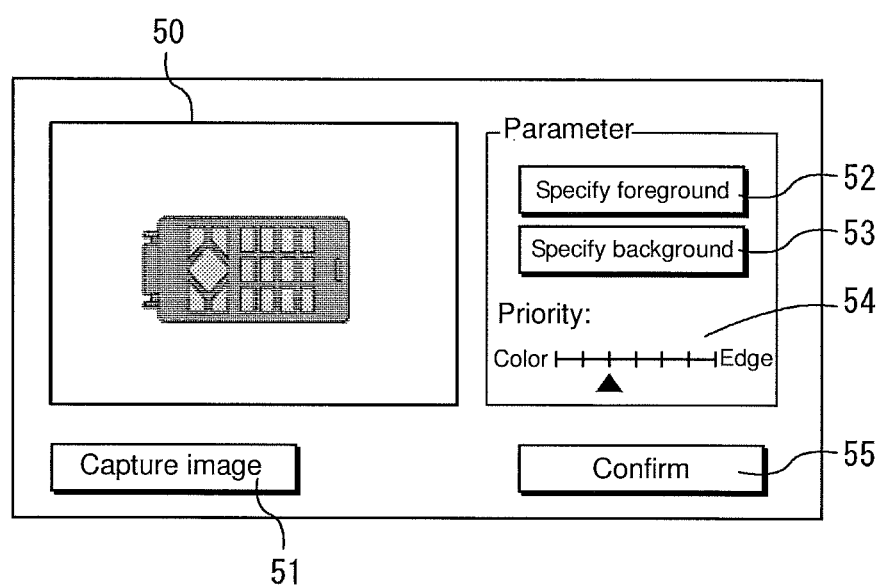
FIG. 5 is a view illustrating an example of an examination region setting screen.

The setting screen in FIG. 5 is displayed on display device 12 when setting tool 103 is started up. Image window 50, image capturing button 51, foreground specifying button 52, background specifying button 53, priority adjusting slider 54, and confirm button 55 are provided in the setting screen. Manipulations such as button selection and slider movement can be performed using input device 14. The setting screen in FIG. 5 is only by way of example, and any UI may be used as long as the following parameter input and examination region confirmation are performed.

When image capturing button 51 is pressed, setting tool 103 captures an image of a sample of the to-be-examined object using image sensor 11 (Step S40). The non-defective to-be-examined object (in the above example, the casing component) is used as the sample, the image of the sample may be captured in the same state (such as a relative position between image sensor 11 and the sample and lighting) as the actual examination process. The obtained sample image data is taken in apparatus body 10. In the case that the previously-captured sample image exists in the auxiliary storage device or storage device 13 of apparatus body 10, setting tool 103 may read the sample image data from the auxiliary storage device or storage device 13.

The sample image obtained in Step S40 is displayed in image window 50 on the setting screen as illustrated in FIG. 5 (Step S41).

In Step S42, the user inputs representative colors (in the case of the monochrome image, representative luminance) of the foreground and the background. The foreground indicates a portion that should be extracted as the examination region, and the background indicates a portion except the examination region. In the case that a foreground representative color is input, the user presses foreground specifying button 52 on the setting screen to put the setting screen in a foreground specifying mode, and the user specifies the portion that should be the foreground on the sample image displayed in image window 50. At this point, the specification is performed to pick up the foreground representative color. In the example of FIG. 5, some pixels or the pixel group in the panel surface of the casing component may properly be selected. In the case that a portion in which a pattern, shading, and the color differ largely from those of other portions is included in the foreground, according to one or more embodiments of the present invention, the pixel group is selected such that these colors are included as much as possible. In the case that a background representative color is input, after background specifying button 53 is pressed to switch the setting screen to a background specifying mode, the similar manipulation is performed. It is not always necessary to input the representative colors of the foreground and the background. One of the foreground and the background may be input, or Step S42 may be eliminated in the case that the representative color is already known or in the case that the representative color can automatically be calculated from a color distribution of the sample image and the like.

In Step S43, based on the representative colors of the foreground and the background, which are specified in Step S42, setting tool 103 segments the sample image into the foreground and the background to select the foreground as the examination region. In one or more embodiments of the present invention, using the information on the edge included in the sample image in addition to the information on the color of each pixel of the sample image, the degree of color separation (the degree of pixel separation) between the foreground and the background (that is, between the inside and the outside of the candidate region) and the degree of overlap (the degree of edge overlap) between the boundary (that is, the contour of the candidate region) of the foreground and the background and the edge in the sample image are comprehensively evaluated with respect to plural candidate regions that are of candidate solutions of the examination region, and the optimum solution is searched such that both the degree of pixel separation and the degree of edge overlap are enhanced. At this point, the same algorithm as the optimum solution search process used to determine the examination region in the examination process (Step S22) is used in the optimum solution search process.

In Step S44, the examination region calculated in Step S43 is displayed in image window 50 on the setting screen.

The user can confirm whether the desired region is selected as the examination region by seeing the examination region displayed on the setting screen. At this point, when the examination region overlaid on the sample image, according to one or more embodiments of the present invention, the to-be-examined object and the examination region are easily compared to each other.

Then setting tool 103 waits for the input from the user (Step S45). In the case that confirm button 55 is pressed, setting tool 103 generates the examination region definition information with respect to the present parameter and stores the examination region definition information in storage device 13 (Step S46). The examination region definition information stored in storage device 13 is used in the examination process. In setting tool 103 of one or more embodiments of the present invention, the parameters such as the foreground representative color, the background representative color, and a priority (balance parameter) between the color information and the edge information are described in the examination region definition information. The color information such as a pixel value and a color histogram may directly be used as the foreground representative color or the background representative color, or information (information in which the color information is modeled) processed from the color information may be used as the parameter. For example, a histogram expressed by a Gaussian mixture model or a histogram modeled using Kernel density estimation may be used as the parameter. The parameter provided as the examination region definition information is not limited to the foreground representative color, the background representative color, and the priority between the color information and the edge information, but any parameter may be provided as long as the parameter acts as the constraint condition in the optimum solution search process.

In the case that the examination region displayed on the setting screen is improper as a result of the optimum solution search process, the user can adjust the parameters by manipulating foreground specifying button 52, background specifying button 53, and priority adjusting slider 54 (Step S47). The evaluation of the degree of pixel separation is influenced when the foreground or background representative color is specified again. When the priority between the color information and the edge information is changed using priority adjusting slider 54, a balance (weight) can be changed in evaluating the degree of pixel separation and the degree of edge overlap. When receiving the input (change) of the parameter from the user, setting tool 103 recalculates the optimum solution of the examination region with the new parameter as the constraint condition, and displays the post-recalculation examination region on the setting screen (Step S47→S43 and S44). The calculation of the examination region can be repeated until the desired result is obtained while the parameter is properly adjusted by this function.

Figure 6:
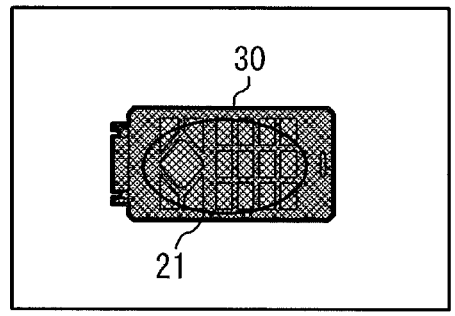
FIG. 6 is a view illustrating an example of a process of narrowing the examination region by parameter adjustment.
Figure 6:
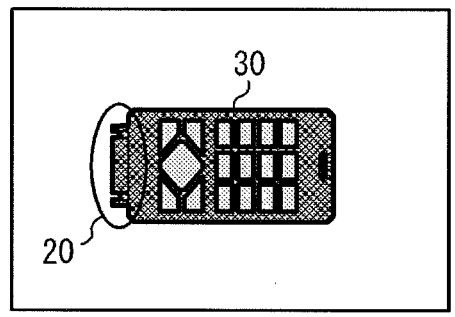
Figure 6:
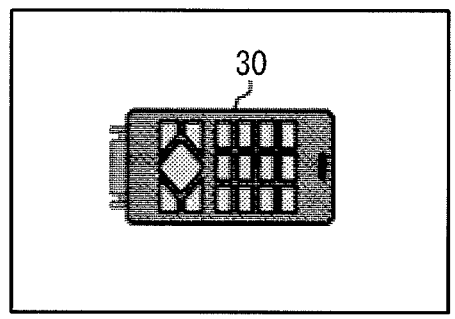
Figure 6:

FIG. 6 illustrates an example of a process of narrowing the parameter. An upper part of FIG. 6 illustrates examination region 30 obtained by an initial calculation. In the initial calculation result, hinge unit 20 and button unit 21 of the casing component are also included in the examination region 30. However, in this case, hinge unit 20 and button unit 21 are excluded from the examination region in order to examine the flaw and the color unevenness of the panel surface (see FIG. 3). At first, the user presses background specifying button 53 to switch the setting screen to the background specifying mode, and additionally specifies the color of button unit 21 in the sample image to the background representative color. Therefore, as illustrated in the middle part of FIG. 6, button unit 21 is excluded from examination region 30. As to hinge unit 20, the balance parameter is adjusted because of the small color difference with the panel surface. That is, attention is focused on the edge in which a step is generated between hinge unit 20 and the panel surface, and the priority for the edge information is increased using priority adjusting slider 54. Therefore, as illustrated in the lower part of FIG. 6, the contour of examination region 30 is set to the edges of hinge unit 20 and the component surface to form desired examination region 30.

(Optimum Solution Search Process)

The optimum solution search process (Step S22 in FIG. 2) in the examination process and the optimum solution search process (Step S43 in FIG. 4) in the examination region setting process are based on the same algorithm. The specific calculation method will be described below.

As described above, in the optimum solution search process of one or more of the embodiments, both the degree of pixel separation between the foreground and the background and the degree of edge overlap at the boundary of the foreground and the background are comprehensively evaluated to obtain the optimum solution from the candidate solutions of the examination region. The calculation can be considered as an optimization problem that minimizes (or maximizes) an objective function including a function evaluating the degree of pixel separation based on the color information and a function evaluating the degree of edge overlap based on the edge information. A technique of solving the optimization problem of the examination region using a graph-cut algorithm will be described below. Because the graph-cut algorithm is the well known technique (for example, see Non-Patent Document 1), the description of a basic concept of the graph-cut algorithm is neglected, and a portion unique to one or more of the embodiments is mainly described below.

In the graph-cut algorithm, an energy function expressed by the following equation is defined as the objective function, and solution L minimizing energy E is obtained when I is provided. In one or more embodiments of the present invention, I is the sample image, and L is a label (that is, examination region) indicating the foreground or the background.

[Mathematical formula 1]

$$E(L \mid I) = \sum_{i \in \Omega} U(l_i \mid I) + \lambda \sum_{\{i,j\} \in N} V(l_i, l_j \mid I) \quad (1)$$

Where i and j are indexes of the pixel, $\Omega$ is a pixel group in image I, and N is an adjacent pixel pair group in image I. li and lj are specifying labels of pixels i and j, respectively. It is assumed that a label of "1" is provided to the foreground while a label of "0" is provided to the background. A first term of the right-hand side is called a data term, and the data term provides the constraint condition related to target pixel i. A second term of the right-hand side is called a smoothing term, and the smoothing term provides the constraint condition related to pixels i and j adjacent to each other. $\lambda$ is a balance parameter that determines the weights (balance) of the data term and the smoothing term.

The data term is defined by a function evaluating the degree of pixel separation based on the color information. For example, evaluation function U of the data term may be defined by the following equation.

[Mathematical formula 2]

$$U(l_i \mid I) = \begin{cases} -\log p(I \mid l_i = 1), & \text{if } l_i = 1 \\ -\log p(I \mid l_i = 0), & \text{if } l_i = 0 \end{cases} \quad (2)$$

Where $-\log p$ (i|ii=1) is a function (logarithmic likelihood) expressing a likelihood of the foreground of the foreground pixel (the pixel to which foreground label "1" is provided) with respect to the foreground representative color, and is called a foreground likelihood. A probability density function (for example, the probability density function in which the color distribution of the foreground representative color is approximated by the Gaussian mixture model) estimated from the foreground representative color is used in the foreground likelihood. On the other hand, $-\log p$ (I|li=0) is a function (logarithmic likelihood) expressing a likelihood of the background of the background pixel (the pixel to which background label "0" is provided) with respect to the background representative color, and is called a background likelihood. A probability density function (for example, the probability density function in which the color distribution of the background representative color is approximated by the Gaussian mixture model) estimated from the background representative color is used in the background likelihood. That is, the data term expresses a summation of the foreground likelihoods of the foreground pixels and a summation of the background likelihoods of the background pixels, energy decreased as the color of the foreground pixel is close to the foreground representative color or as the color of the background pixel is close to the background representative color, and the energy increases as the color of the foreground pixel separates from the foreground representative color or as the color of the background pixel separates from the background representative color.

The smoothing term is defined by a function evaluating the degree of edge overlap based on the edge information. For example, evaluation function V of the smoothing term can be defined by the following equation.

[Mathematical formula 3]

$$V(l_i, l_j \mid I) = \begin{cases} \exp\{-\beta \|l_i - l_j\|^2\}, & \text{if } l_i \neq l_j \\ 0, & \text{if } l_i = l_j \end{cases}$$

Where li and lj are pixel values (color or luminance) of pixels i and j, and $\beta$ is a coefficient. $\|li-lj\|^2$ expresses a difference (distance) of the pixel values on a predetermined color space, namely, a height of contrast between the pixels.

According to the equation (3), in the case that adjacent pixels i and j differs from each other in the label, the energy increases for the low contrast between pixels i and j, and the energy decreases for the high contrast between pixels i and j. The portion having the high contrast between the adjacent pixels is a portion in which the color or the luminance in the image changes largely, namely, the edge portion in the image. That is, in the equation (3), the energy decreases as the boundary (pixel pair having different labels) of the foreground and the background overlaps the edge in the image.

In the above energy function, a global minimum exists in the case that a given submodularity is satisfied. Similarly, the global minimum can be obtained with the constraint condition by adding a term satisfying the submodularity. A well-known search algorithm may be used in an efficient method for solving the global minimum, the detailed description is neglected.

In the parameters that can be adjusted on the setting screen, "the foreground representative color" and "the background representative color" have an influence on the value of the data term. "The priority between the color information and the edge information" corresponds to balance parameter $\lambda$. When the user increases the priority for the color information, the value of parameter $\lambda$ is decreased to increase the weight of the data term. When the user increases the priority for the edge information, the value of parameter $\lambda$ is increased to increase the weight of the smoothing term. The value of parameter $\lambda$ can automatically be determined with a calculator (setting tool 103). For example, setting tool 103 calculates a difference between the foreground representative color and the background representative color, and the value of parameter $\lambda$ is decreased to increase the weight of the data term when the difference is large. This is because the data term can be estimated to have high reliability in the case that there is a clear color different between the foreground and the background. On the other hand, the value of parameter $\lambda$ is increased to increase the weight of the smoothing term when the difference between the foreground representative color and the background representative color is small. This is because the better result tends to be obtained in the region segmentation based on the edge information rather than the color information in the case that there is an unclear color different between the foreground and the background. The automatic adjustment of balance parameter $\lambda$ can enhance a probability that can reach a valid solution without the user support. According to one or more embodiments of the present invention, an initial value of balance parameter $\lambda$ is automatically determined by the above method, and the user adjusts balance parameter $\lambda$ (the priority between the color information and the edge information) with the initial value as a starting point. This is because, with increasing validity of the initial value, the number of trial and error times of the user can be decreased and a work load on the parameter adjustment can be expected to be reduced.

In the equation (2), the summation of the likelihood (foreground likelihood) of the foreground of the foreground pixel and the likelihood (background likelihood) of the background of the background pixel is used as the data term. However, the evaluation function of the degree of pixel separation is not limited to the summation of the foreground likelihood and the background likelihood. For example, a product, a weighted sum, a weighted product, a nonlinear function sum, a nonlinear function product of the likelihood of the foreground and the likelihood of the background may be used. A monotonically increasing function may be used as the nonlinear function. Both the likelihood of the foreground and the likelihood of the background are not evaluated, but only the likelihood of the foreground or only the likelihood of the background may be evaluated and used as the degree of pixel separation. Specifically, a function in which U (li|I)=0 is obtained for li=0 (or for li=1) can be used in the equation (2). The following equation (4) is one that evaluates only the likelihood of the foreground.

[Mathematical formula 4]

$$U(l_i \mid I) = \begin{cases} -\log p(I \mid l_i = 1), & \text{if } l_i = 1 \\ 0, & \text{if } l_i = 0 \end{cases}$$

In calculating the likelihood of the foreground, all the foreground pixels (that is, all the pixels inside the candidate region) may be used, or only some foreground pixels may be used. Similarly, in calculating the likelihood of the background, all the background pixels (that is, all the pixels outside the candidate region) may be used, or only some background pixels may be used. For example, the pixel in which the label is confirmed is excluded from the calculation, or only the pixels located within a predetermined distance from the contour of the candidate region are used in the calculation, which allows a calculation time to be shortened.

The function evaluating the likelihood of the foreground or the likelihood of the background is not limited to the equation (2). For example, a likelihood ratio that is of a ratio of the foreground likelihood and the background likelihood can be used as expressed by the following equation.

[Mathematical formula 5]

$$U(l_i \mid I) = \begin{cases} -\log \dfrac{p(I \mid l_i = 1)}{p(I \mid l_i = 0)}, & \text{if } l_i = 1 \\ -\log \dfrac{p(I \mid l_i = 0)}{p(I \mid l_i = 1)}, & \text{if } l_i = 0 \end{cases}$$

Using directly the histogram of the pixel group specified as the foreground representative color by the user (without estimating the probability density function), the likelihood of the foreground may be evaluated based on a degree of similarity of the color of each pixel with respect to the foreground representative color histogram, or the likelihood of the background may be evaluated based on a degree of difference of the color of each pixel with respect to the foreground representative color histogram. Similarly, the likelihood of the background may be evaluated based on the degree of similarity to the histogram (background representative color histogram) of the pixel group specified as the background representative color by the user, or the likelihood of the foreground may be evaluated based on the degree of difference from the background representative color histogram. Alternatively, the degree of similarity or the degree of difference between a foreground histogram obtained from the foreground pixel group of the candidate region or a background histogram obtained from the background pixel group and the foreground representative color histogram or the background representative color histogram may be calculated using a predetermined function or a distance index. Alternatively, the histogram approximated from the information on the color or the luminance of the pixel group, and the degree of similarity or the degree of difference may be calculated using the approximated histogram.

(Additional Parameter)

In one or more embodiments of the present invention, the three parameters, namely, the foreground representative color, the background representative color, and the priority between the color information and the edge information are described. Additionally, any parameter may be used as long as the parameter has the influence on the optimum solution search of the examination region. For example, because the appearance examination is mainly aimed at industrial products, frequently the shape, a texture, and topology of the portion constituting the examination region, an element adjacent to the examination region, or an element included in the examination region has the feature. The image sensor is installed such that the to-be-examined object just falls within the angle of view, a size or the position in the image of the portion constituting the examination region can be predicted to some extent. Therefore, the user is caused to input the information indicating the feature of the examination region as the parameter, and the constraint condition evaluating the degree of similarity between the feature provided by the parameter and the feature of the examination region is added to the objective function, which allows a further enhancement of a possibility of searching the valid examination region. In the case that the parameter is newly added, the value of the parameter is also included in the examination region definition information.

For example, the basic shape (such as a circular shape, rectangular shape, a triangular shape, and a star shape) of the examination region and the feature (such as a linear outer shape, a round outer shape, and a jagged shape) of the contour can be used as shape information expressing the feature related to the shape of the examination region. As to a UI used to input the shape information, a list of templates of the basic shapes or the features of the contours is displayed, and the user is caused to select the corresponding template or feature. For example, the following equation may be inserted as the constraint condition in the case that the template of the basic shape is specified.

[Mathematical formula 6]

$$\min \log \sum_i \|l_i - T(t_i)\|^2$$

Where li is a specifying label of pixel i and ti is a label at a point corresponding to pixel i on the template. T ( ) expresses an affine transformation. The equation (6) expresses a manipulation that, while enlarging/reducing, rotating, or deforming the specified template, performs template matching to the candidate region, and calculates a minimum score. That is, the energy decreases in the region having the shape close to the basic shape specified by the user by adding the constraint condition of the equation (6), and the region is preferentially selected as the optimum solution.

For example, the following equation may be inserted as the constraint condition in the case that a degree of jaggy or a degree of smoothness is specified as the feature of the contour.

[Mathematical formula 7]

$$\log \left\{ \left\| \sum \left| \frac{\partial \theta}{\partial S} \right| - C \right\|^2 \right\}$$

Where S is a point on the contour of the foreground region, θ is a slope angle of the contour, and ∂θ/∂s expresses an amount of change in slope angle along the contour of the foreground region. C is a constant indicating the degree of jaggy (the degree of smoothness) specified by the user. The value of C increases with increasing degree of jaggy, and the value of C decreases with increasing degree of smoothness. The equation (7) is a function evaluating whether a total value (expressing the degree of jaggy of the contour) of the amount of change in slope angle of the contour in the foreground region is close to value C (expressing the specified degree of jaggy). That is, the region having the contour feature close to the degree of jaggy specified by the user is preferentially selected as the optimum solution by adding the constraint condition of the equation (7).

An area and horizontal and vertical lengths of the examination region can be used as size information expressing the feature related to the size of the examination region. For example, the following equation may be inserted as the constraint condition in the case that the area is input as the size information.

[Mathematical formula 8]

$$\log \left\{ \left\| \sum_i l_i - C \right\|^2 \right\}$$

Where C is an area (the number of pixels) of the foreground region specified by the user. Because the foreground label is 1 while the background label is 0, Σli expresses the summation of the foreground pixels, namely, the area of the foreground region. Accordingly, the equation (8) is a function evaluating whether the area of the foreground region is close to specified area C. The region having the size close to the area specified by the user is preferentially selected as the optimum solution by adding the constraint condition of the equation (8).

For example, a barycentric coordinate of the examination region and an existence range (such as up, down, right, left, center) of the examination region can be used as position information expressing the feature related to the position of the examination region in the image. For example, the following equation may be inserted as the constraint condition in the case that the barycentric coordinate is input as the position information.

$$\log \{\|w - C\|^2\}$$ [Mathematical formula 9]

Where w is a barycentric coordinate of the foreground region and C is a barycentric coordinate specified by the user. The equation (9) is a function evaluating whether the barycentric coordinate of the foreground region is close to specified coordinate C. The region having the barycenter at the position close to the coordinate specified by the user is preferentially selected as the optimum solution by adding the constraint condition of the equation (9).

For example, information expressing the pattern in the examination region, the shading of the color, irregularity, or a material can be used as texture information expressing the feature related to the texture of the examination region. For example, a list of various texture templates is displayed, and the user may be caused to select the corresponding texture template. For example, the following equation may be inserted as the constraint condition in the case that the texture template is input.

$$\log f(h_{l=1}(I) - h_{l=1}(E))$$ [Mathematical formula 10]

Where I is a sample image and E is a texture template specified by the user. $h_{l=1}(\ )$ expresses a color histogram of the foreground pixel, and f ( ) is a function indicating the degree of similarity of the histogram. That is, the equation (10) is a function evaluating whether the color histogram of the foreground region in the sample image is similar to the color histogram of the specified texture. The region having the texture similar to that specified by the user is preferentially selected as the optimum solution by adding the constraint condition of the equation (10).

In image examination apparatus 1 of one or more embodiments of the present invention, the examination region obtained from the sample image is not directly used in the examination process, but the parameter (constraint condition), which is used in the process of obtaining the optimum solution of the examination region from the sample image, is provided to image examination apparatus 1. At the stage of the examination process, image examination apparatus 1 reads the parameters from the storage device and performs the optimum solution search process using the parameters, thereby the position or the shape of the examination region is determined in each to-be-examined object. Accordingly, the correct examination region can automatically be set to the to-be-examined object having the complicated shape or the special shape, and the correct examination region can adaptively and automatically be set even if the to-be-examined object has the individual difference or even if the position or the orientation of the to-be-examined object is indefinite. In one or more embodiments of the present invention, the use of the algorithm that comprehensively evaluates the both the degree of pixel separation and the degree of edge overlap using the edge information in addition to the color or luminance information can improve the region extraction accuracy compared with conventional techniques such as the binarization and the gamut extraction. Therefore, in image examination apparatus 1 of one or more embodiments of the present invention, a wide variety of to-be-examined objects can be dealt with, and the examination can be performed with high accuracy than ever before.

Setting tool 103 of one or more embodiments of the present invention can cause the user to arbitrarily select the priority between the color information and the edge information on the setting screen. For example, in the case that the image includes many pseudo-contours such that the pattern is included in the foreground or the background, there is a high possibility of obtaining the better result when the preference is given to the color or luminance information over the edge information. In the case that the color of the foreground is similar to that of the background, there is a high possibility of obtaining the better result when the preference is given to the edge information over the color or luminance information. In the image in which the foreground and the background are hardly segmented, it is difficult to reach the correct solution in the completely automatic manner. At the same time, the user can easily see the image to decide which one of the color or luminance information and the edge information the preference is given to, and the user can easily narrow the parameter by the trial and error. Accordingly, like the configuration of one or more embodiments of the present invention, the balance parameter can be adjusted to produce the examination region definition information simply obtaining the desired examination region in a short time.

The embodiments of the present invention are described only by way of example, and the scope of the present invention is not limited to the embodiment. For example, the color information on the image is used because the color image is considered in one or more of the above embodiments. For the use of the monochrome image, the luminance information may be used instead of the color information. In one or more of the above embodiments, the graph-cut algorithm is used in the optimization. Alternatively, other methods such as a level-set algorithm may be used. In other methods, the examination region can also accurately be calculated using the color information (luminance information) and the edge information. At this point, preferably the user can change the priority between the color information (luminance information) and the edge information.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF SYMBOLS

1: image examination apparatus
2: to-be-examined object (casing component)
10: apparatus body
11: image sensor
12: display device
13: storage device
14: input device
101: examination processor
102: examination region extracting unit
103: setting tool
20: hinge unit
21: button unit
30: examination region
31: examination region image
50: image window
51: image capturing button
52: foreground specifying button
53: background specifying button
54: priority adjusting slider
55: confirm button

The invention claimed is:

1. An image examination method comprising:
an acquisition step of acquiring a to-be-examined object image obtained by capturing an image of a to-be-examined object;
a setting reading step of reading an examination region definition information from a storage device in which the examination region definition information is previously stored;
an examination region extracting step of extracting a portion constituting the examination region as an examination region image from the to-be-examined object image based on the examination region definition information; and
an examination process step of examining the to-be-examined object by analyzing the examination region image,
wherein the examination region definition information is a parameter used as a constraint condition in an optimum solution search process,
wherein, in the examination region extracting step, a position and a shape of the examination region are separately determined in each to-be-examined object by performing an optimum solution search process of obtaining an optimum solution of the examination region in the to-be-examined object image with the parameter as the constraint condition,
wherein the optimum solution search process is a process of obtaining an optimum solution of the examination region in a plurality of candidate regions, which are of candidate solutions of the examination region, by evaluating both a degree of pixel separation and a degree of edge overlap based on information a color or a luminance of each pixel in the to-be-examined object image and information on an edge comprised in the to-be-examined object image, and
wherein the degree of pixel separation is a degree of separation of the color or the luminance between an inside and an outside of each candidate region, the degree of edge overlap being a degree of overlap between a contour of each candidate region and the edge in the to-be-examined object image.

2. The image examination method according to claim 1, wherein the examination region definition information comprises a balance parameter as the parameter,
wherein the balance parameter is used to adjust a weight in evaluating the degree of pixel separation and the degree of edge overlap.

3. The image examination method according to claim 1, wherein one of a value of foreground likelihood of the color or the luminance of each pixel inside the candidate region with respect to a representative color or a representative luminance of a foreground, a value of background likelihood of the color or the luminance of each pixel outside the candidate region with respect to a representative color or a representative luminance of a background, and a synthesizing value of both the values is used as the degree of pixel separation in the optimum solution search process.

4. The image examination method according to claim 3, wherein the examination region definition information comprises information on one of the representative color and the representative luminance of one of the foreground, the background, and the both as the parameter.

5. The image examination method according to claim 1, wherein the examination region definition information comprises shape information expressing a feature related to the shape of the examination region as the parameter, and
wherein, in the optimum solution search process, the optimum solution of the examination region is obtained such that a degree of similarity between the shape of the examination region and the shape expressed by the shape information is also enhanced in addition to the degree of pixel separation and the degree of edge overlap.

6. The image examination method according to claim 1, wherein the examination region definition information comprises size information expressing the feature related to a size of the examination region as the parameter,
wherein, in the optimum solution search process, the optimum solution of the examination region is obtained such that a degree of similarity between the size of the examination region and the size expressed by the size information is also enhanced in addition to the degree of pixel separation and the degree of edge overlap.

7. The image examination method according to claim 1, wherein the examination region definition information comprises position information expressing the feature related to a position of the examination region in the image as the parameter,
wherein, in the optimum solution search process, the optimum solution of the examination region is obtained such that a degree of similarity between the position of the examination region in the image and the position expressed by the position information is also enhanced in addition to the degree of pixel separation and the degree of edge overlap.

8. The image examination method according to claim 1, wherein the examination region definition information comprises texture information expressing the feature related to a texture of the image in the examination region as the parameter,
wherein, in the optimum solution search process, the optimum solution of the examination region is obtained such that a degree of similarity between the texture of the image in the examination region and the texture expressed by the texture information is also enhanced in addition to the degree of pixel separation and the degree of edge overlap.

9. The image examination method according to claim 1, further comprising:
an examination region definition information setting step of generating the examination region definition information and storing the examination region definition information in the storage device before the examination of the to-be-examined object is started,
wherein the examination region definition information setting step comprises:
acquiring a sample image obtained by capturing an image of a sample of the to-be-examined object;
receiving input of the parameter from a user;
narrowing the parameter being able to obtain a desired examination region in the sample image in a manner that, every time the input of the parameter is received from the user, the optimum solution search process is performed to the sample image while the constraint condition is updated based on the input parameter; and
storing the parameter, which is used to be able to obtain the desired examination region in the sample image, in the storage device as the examination region definition information.

10. A program stored on a non-transitory computer readable medium that causes a computer to perform an image examination method comprising:
an acquisition step of acquiring a to-be-examined object image obtained by capturing an image of a to-be-examined object;
a setting reading step of reading an examination region definition information from a storage device in which the examination region definition information is previously stored;
an examination region extracting step of extracting a portion constituting the examination region as an examination region image from the to-be-examined object image based on the examination region definition information; and
an examination process step of examining the to-be-examined object by analyzing the examination region image,
wherein the examination region definition information is a parameter used as a constraint condition in an optimum solution search process,
wherein, in the examination region extracting step, a position and a shape of the examination region are separately determined in each to-be-examined object by performing an optimum solution search process of obtaining an optimum solution of the examination region in the to-be-examined object image with the parameter as the constraint condition,
wherein the optimum solution search process is a process of obtaining an optimum solution of the examination region in a plurality of candidate regions, which are of candidate solutions of the examination region, by evaluating both a degree of pixel separation and a degree of edge overlap based on information a color or a luminance of each pixel in the to-be-examined object image and information on an edge comprised in the to-be-examined object image, and
wherein the degree of pixel separation is a degree of separation of the color or the luminance between an inside and an outside of each candidate region, the degree of edge overlap being a degree of overlap between a contour of each candidate region and the edge in the to-be-examined object image.

11. An image examination apparatus comprising:

an acquisition unit that acquires a to-be-examined object image obtained by capturing an image of a to-be-examined object;

a setting reading unit that reads an examination region definition information from a storage device in which the examination region definition information is previously stored;

an examination region extracting unit that extracts a portion constituting an examination region as the examination region image from the to-be-examined object image based on the examination region definition information; and an examination process unit that examines the to-be-examined object by analyzing the examination region image, wherein the examination region definition information is a parameter used as a constraint condition in an optimum solution search process, wherein the examination region extracting unit separately determines a position and a shape of the examination region in each to-be-examined object by performing an optimum solution search process of obtaining an optimum solution of the examination region in the to-be-examined object image with the parameter as the constraint condition, wherein the optimum solution search process is a process of obtaining an optimum solution of the examination region in a plurality of candidate regions, which are of candidate solutions of the examination region, by evaluating both a degree of pixel separation and a degree of edge overlap based on information a color or a luminance of each pixel in the to-be-examined object image and information on an edge comprised in the to-be-examined object image, and wherein the degree of pixel separation is a degree of separation of the color or the luminance between an inside and an outside of each candidate region the degree of edge overlap being a degree of overlap between a contour of each candidate region and the edge in the to-be-examined object image.

* * * * *